United States Patent
Steinman et al.

(10) Patent No.: US 9,629,359 B2
(45) Date of Patent: Apr. 25, 2017

(54) CANNULA WITH FLOATING CLAMPING MEMBER

(71) Applicant: LIFELINE SCIENTIFIC, INC., Itasca, IL (US)

(72) Inventors: Christopher P. Steinman, Sandy, UT (US); Jason A. Belton, Norton, OH (US); Kirk C. Palmerton, Kent, OH (US); Karl H. Beitzel, Canton, OH (US); Rick W. Walker, Stow, OH (US); Matthew Copithorne, Framingham, MA (US); Brian Otts, Warrior, AL (US); James V. Guarrera, New York, NY (US)

(73) Assignee: LIFELINE SCIENTIFIC, INC., Itasca, IL (US)

( * ) Notice: Subject to any disclaimer, the term of this patent is extended or adjusted under 35 U.S.C. 154(b) by 141 days.

(21) Appl. No.: 14/335,393

(22) Filed: Jul. 18, 2014

(65) Prior Publication Data
US 2014/0329220 A1    Nov. 6, 2014

Related U.S. Application Data

(62) Division of application No. 13/545,185, filed on Jul. 10, 2012, now Pat. No. 8,814,889.

(51) Int. Cl.
| | |
|---|---|
| *A61B 17/28* | (2006.01) |
| *A01N 1/02* | (2006.01) |
| *A61B 17/122* | (2006.01) |
| *A61B 17/00* | (2006.01) |

(52) U.S. Cl.
CPC .......... *A01N 1/0247* (2013.01); *A61B 17/122* (2013.01); *A61B 17/28* (2013.01); *A61B 2017/00907* (2013.01); *A61B 2017/00969* (2013.01); *A61B 2017/2808* (2013.01)

(58) Field of Classification Search
CPC .............................. A61B 17/122; A61B 17/28
See application file for complete search history.

(56) References Cited

U.S. PATENT DOCUMENTS

| | | |
|---|---|---|
| 1,339,419 A | 5/1920 | Rea |
| 1,339,420 A | 5/1920 | Rea |
| 1,566,653 A | 12/1925 | Crotto |
| 2,262,162 A | 11/1941 | Bock |
| 3,709,526 A | 1/1973 | Cromie |
| 4,389,034 A | 6/1983 | Suttles |

(Continued)

*Primary Examiner* — Dianne Dornbusch
(74) *Attorney, Agent, or Firm* — Oliff PLC

(57) ABSTRACT

A cannula has a longitudinal base member having a first clamping end and a longitudinal arm member pivotally attached to the longitudinal base member and having a second clamping end, the cannula being in a closed position when the first and second clamping ends are brought together. A first clamp member is located at the first clamping end and has a first passage. A second clamp member is rotatably attached to the arm member at the second clamping end and has a second passage. The first and second passages form a combined passage when the clamp is in the closed position. The cannula may have a first locking member positioned on the arm member and a second locking member positioned on the base member. The first and second locking members interact with each other to lock the cannula in the closed position.

9 Claims, 7 Drawing Sheets

(56) References Cited

U.S. PATENT DOCUMENTS

| | | | |
|---|---|---|---|
| 4,437,791 A | | 3/1984 | Reynolds |
| 5,571,125 A | | 11/1996 | Chadwick |
| 5,582,082 A | | 12/1996 | Gajo |
| 5,728,115 A | * | 3/1998 | Westcott ............. A61B 17/122 604/250 |
| 6,871,570 B1 | | 3/2005 | Santillan |
| 6,899,262 B2 | | 5/2005 | Gaunekar et al. |
| 7,559,525 B2 | | 7/2009 | Grimes |
| 7,588,585 B2 | | 9/2009 | Gold et al. |
| 7,736,371 B2 | | 6/2010 | Schoepp |
| 7,824,848 B2 | | 11/2010 | Owen et al. |
| 8,105,362 B2 | | 1/2012 | Duarte |
| 8,361,108 B2 | | 1/2013 | Gold et al. |
| 8,382,474 B2 | | 2/2013 | Boltanski et al. |
| 2004/0111104 A1 | * | 6/2004 | Schein .................. A61B 17/00 606/153 |
| 2006/0217746 A1 | | 9/2006 | Krolman |
| 2007/0208223 A1 | | 9/2007 | Julian et al. |
| 2009/0248026 A1 | | 10/2009 | Draper |
| 2010/0096570 A1 | | 4/2010 | Kashmirian et al. |
| 2010/0173258 A1 | | 7/2010 | Boltanski et al. |
| 2010/0268161 A1 | | 10/2010 | Traversaz |
| 2011/0172717 A1 | | 7/2011 | Miller |
| 2012/0095509 A1 | | 4/2012 | Jensen et al. |
| 2012/0143269 A1 | | 6/2012 | Ichelmann et al. |
| 2012/0276519 A1 | | 11/2012 | Kravitz et al. |
| 2012/0277681 A1 | | 11/2012 | Kravitz et al. |
| 2012/0277687 A1 | | 11/2012 | Kravitz et al. |
| 2013/0006198 A1 | | 1/2013 | Traversaz |

* cited by examiner

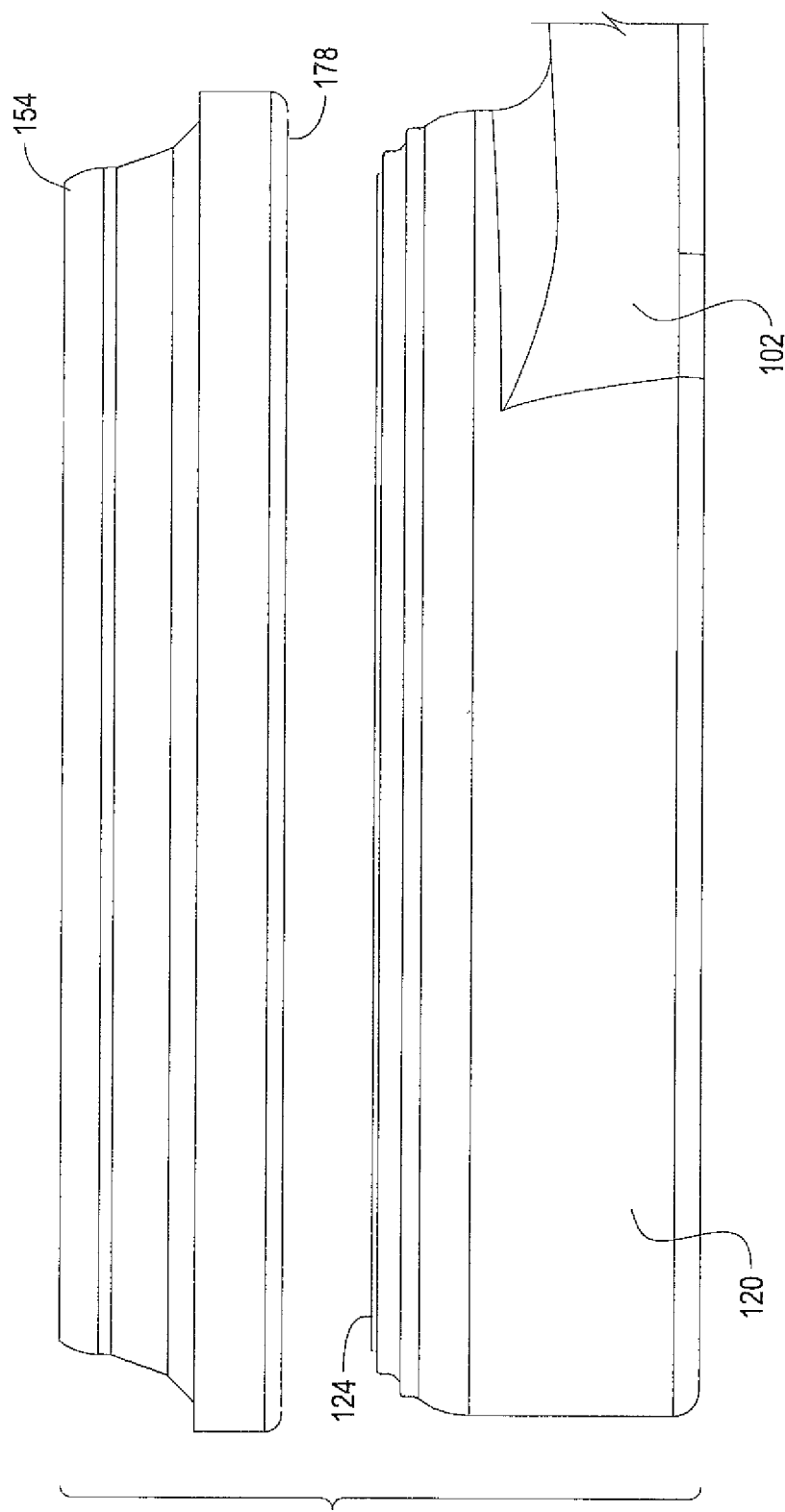

CANNULA WITH FLOATING CLAMPING MEMBER

RELATED APPLICATION

This application is a Divisional of U.S. Pat. No. 8,814,889, filed Jul. 10, 2012. This disclosure of this prior patent is herein incorporated by reference.

BACKGROUND

Related technical fields include cannulas and clamping methods including cannulas and clamping methods for perfusing one or more organs or tissue to monitor, treat, sustain and/or restore the viability of the organ(s) or tissue and/or for transporting and/or storing the organ(s) or tissue.

Various devices have been developed that couple the anatomy of an organ being perfused to a perfusion machine or other equipment such as that described in U.S. Pat. No. 7,824,848, the entire disclosure of which is hereby incorporated by reference. Such devices are typically referred to as perfusion clamps or simply cannulas. Although the term cannula in general use has other meanings, the term cannula is used generically throughout this specification to refer to a clamp or other device that provides a connection through which fluid flow may be established.

A type of cannula as described in U.S. Pat. No. 5,728,115 to Westcott et al. is shown in FIGS. 1-3. A clamping device (cannula) 10 is used to couple a perfusion device to the renal aorta 34. The clamp 10 includes two longitudinal members 12 and 14 which pivot about a pin 16. The proximal end of the member 12 includes an integral handle 18, while the proximal end of the member 14 includes an integral handle 20. The distal end of the member 12 includes an elongated, hollow, annular, integral clamp head 24, while the distal end of the member 14 includes an elongated, hollow, annular, integral clamp head 26. Clamp head 26 includes a nipple 28 attached thereto. Movement of the handles 18 and 20 toward one another forces the members 12 and 14 to pivot about the pin 16, thereby forcing the clamp heads 24 and 26 of the members 12 and 14 away from one another. A spring 22 is positioned between the handles 18 and 20 in order to bias the handles apart. This, in turn, tends to force the clamp heads 24 and 26 together. Therefore, the clamp heads 24 and 26 of the distal ends of the members 12 and 14 are engaged in a clamping relationship unless an external compressive force is applied to the handles 18 and 20. A lumen 32 extends through the nipple 28.

In use, the clamp 10 is attached to a blood vessel of a donor organ such as the renal aorta 34 of a kidney 36 by opening the clamp 10, passing the distal end 38 of the renal aorta 34 through the annular clamp head 24, holding the distal end 38 of the renal aorta 34 over the annular clamp head 24, and releasing pressure on the handles of the clamp 10 in order to allow the clamp head 26 to engage the distal end 38 of the renal aorta 34 against the annular clamp head 24. A catheter 40 may then be attached to the nipple 28 in order to provide perfusion of liquid through the lumen 32 and into the renal aorta 34.

SUMMARY

In the cannula described above, the orientation of the clamp heads 24 and 26 with respect to each other is fixed because the clamp heads 24 and 26 are integral to the members 12 and 14, respectively. Accordingly, the force applied to the tissue during the clamping process may be unevenly distributed across the surface of the tissue, thereby potentially resulting in damage to the tissue or an inadequate grip that is susceptible to failure. In addition, although the cannula shown in FIGS. 1-3 is biased in the closed or clamping position by the spring 22, the cannula does not include a locking mechanism to prevent the cannula from opening at an undesired time. Also, the cannula shown in FIGS. 1-3 provides poor visibility of the vasculature because of a limited range of movement and because the clamp heads 24 and 26 are made of an opaque material (typically metal). The limited range of movement also limits access to the clamp heads 24 and 26, increasing difficulty of use. Further, the nipple 28 may be susceptible to leaks due to a relatively smooth construction and the spring 22 does not allow for adjustment of the force applied to clamped tissue.

In exemplary embodiments, a clamp such as a cannula includes a longitudinal base member and a longitudinal arm member pivotally attached to the longitudinal base member. The clamp also includes a first clamp member at a first end of the base member and a second clamp member pivotally attached to the arm member at a first end of the arm member, the first clamp member opposing the second clamp member. The second clamp member may be movable in more rotational axes and/or more rotational directions with respect to the arm member than the arm member is movable with respect to the base member. In addition, the second clamp member may have one or more than one degree of freedom of movement relative to the arm member, for example, two rotatable degrees of freedom with respect to the arm member.

Pivotally attaching the second clamp member to the arm member allows for force applied to the tissue during the clamping process to be more evenly distributed, thereby reducing damage to the tissue. In addition, the grip on the tissue may be less likely to fail. Also, pivotally attaching the second clamp member to the arm member may allow the a first clamping surface to have a variable position relative to a second clamping surface when the arm member and the base member are held in place with respect to one another.

In exemplary embodiments, a clamp such as a cannula includes a longitudinal base member having a first clamping end and a longitudinal arm member pivotally attached to the longitudinal base member and having a second clamping end. The clamp is in a closed position when the first and second clamping ends are brought together. The clamp also includes a first locking member positioned on the arm member and a second locking member positioned on the base member. The first and second locking members interact with each other to releasably lock the clamp in the closed position.

In exemplary embodiments, a clamp such as a cannula includes a longitudinal base member having a first clamping end and a longitudinal arm member pivotally attached to the longitudinal base member and having a second clamping end, the clamp being in a closed position when the first and second clamping ends are brought together. The clamp also includes a first clamp member at a first end of the base member and a second clamp member movably (e.g., pivotally) attached to the arm member at a first end of the arm member, the first end of the arm member opposing the first end of the base member. In addition, the clamp includes a first locking member positioned on the arm member and a second locking member positioned on the base member. The first and second locking members interact with each other to releasably lock the clamp in the closed position.

In exemplary embodiments, a method of clamping or cannulating a blood vessel includes clamping the blood vessel between a first clamp surface that applies a first force on the blood vessel and a second clamp surface that applies a second force on the blood vessel. A magnitude of the first force is substantially consistent over an entire surface of the blood vessel that is in contact with the first and second clamp surfaces. Clamping or cannulating the blood vessel may facilitate a connection between the blood vessel and a perfusion apparatus.

BRIEF DESCRIPTION OF THE DRAWINGS

Exemplary implementations can be described with reference to the following figures wherein:

FIG. 9 illustrates exemplary clamping surfaces of the clamping apparatus of FIGS. 4 and 5.

DETAILED DESCRIPTION OF EMBODIMENTS

Figure 4:
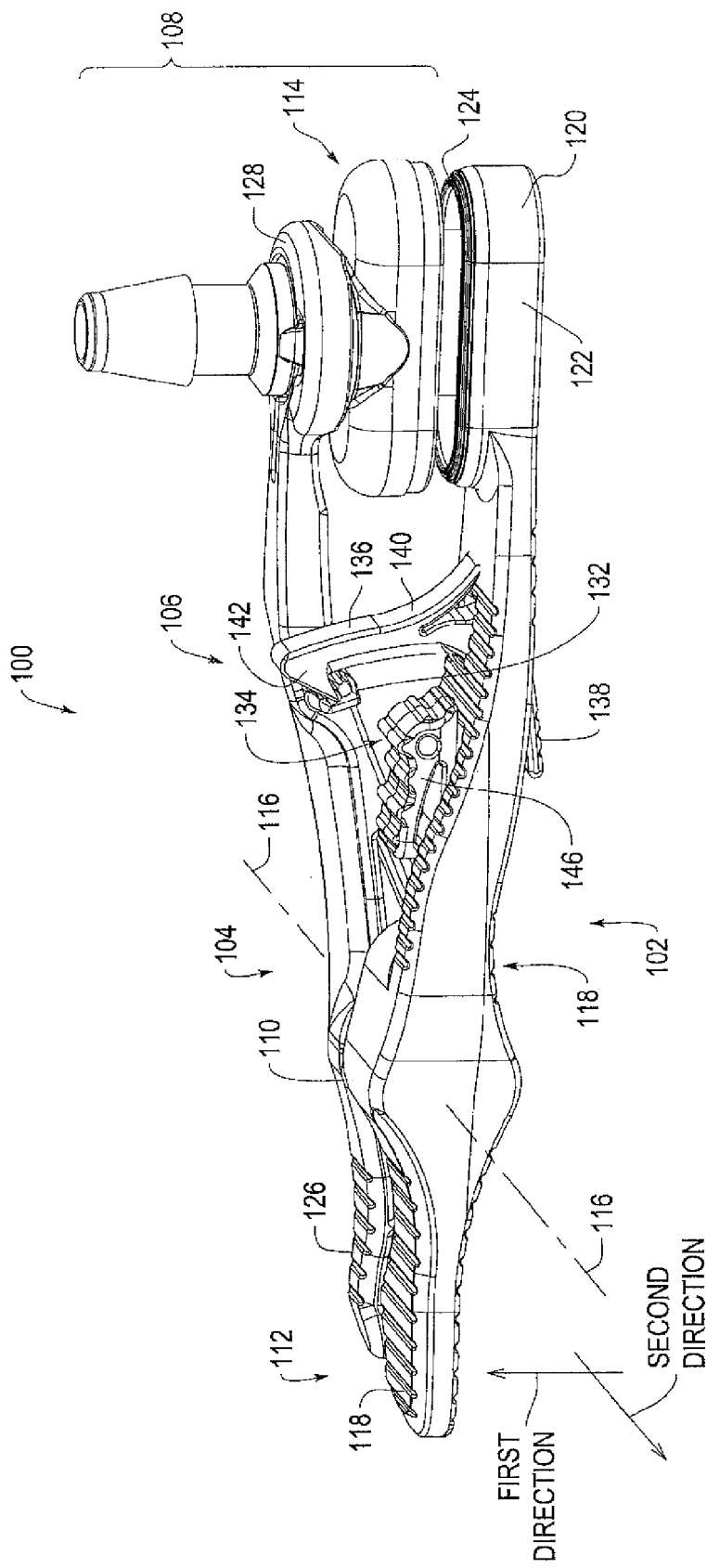
FIG. 4 illustrates an exemplary clamping apparatus in a closed position.

FIG. 4 shows a perfusion clamping apparatus or cannula 100 according to exemplary embodiments. The cannula 100 is capable of connecting one or more blood vessels of an organ or tissue to a perfusion machine or system (not shown) such as that described in U.S. Pat. No. 7,824,848, the entire disclosure of which is hereby incorporated by reference, for example, by connection to tubing of the perfusion machine or system. All medical fluid contact surfaces are preferably formed of or coated with materials compatible with the medical fluid used, preferably non-thrombogenic materials. For convenience, the term "organ" will be used herein to mean organ and/or tissue, except as otherwise specified.

The medical fluid for perfusion may be any suitable medical fluid. For example, it may be a simple crystalloid solution, or may be augmented with an appropriate oxygen carrier. The oxygen carrier may, for example, be washed, stabilized red blood cells, cross-linked hemoglobin, pegolated hemoglobin or fluorocarbon based emulsions. The medical fluid may also contain antioxidants known to reduce peroxidation or free radical damage on the physiological environment and specific agents known to aid in tissue protection. Further, the medical fluid may be or include blood or blood products.

Figure 5:
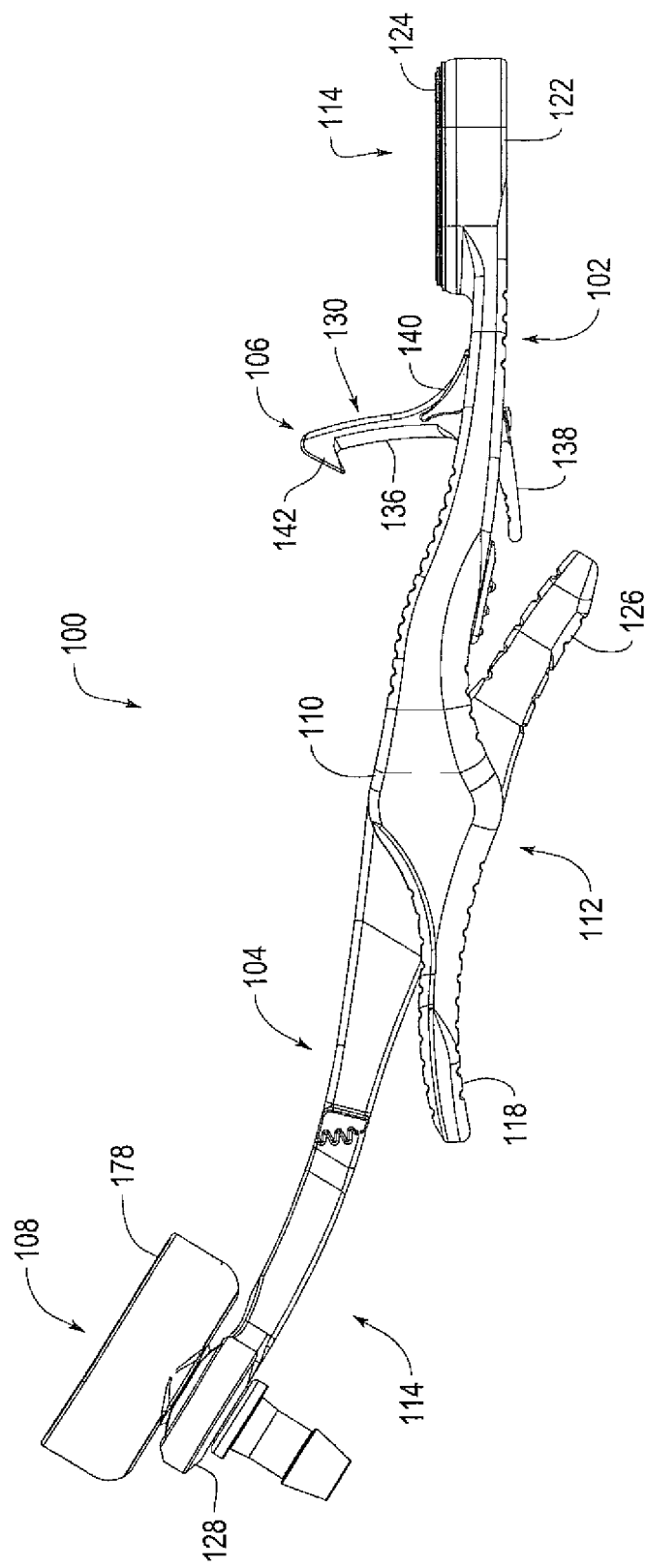
FIG. 5 illustrates an exemplary clamping apparatus of FIG. 4 in an open position.

The cannula 100 is shown in FIG. 4 in a closed or clamping condition and in FIG. 5 in an open condition. The cannula 100 may comprise a base 102, an arm 104, an optional locking mechanism 106 and a floating clamp member 108. Although the floating clamp member 108 is illustrated as being attached to the arm 104, it is contemplated that the floating clamp member 108 may be attached to the base 102 instead of the arm 104. It is further contemplated that the base 102 and the arm 104 may both be attached to respective floating clamp members 108. The base 102 and the arm 104 may be pivotably connected via a pivot mechanism 110. As illustrated, the pivot mechanism 110 may be a pin about which one or both of the base 102 and the arm 104 can rotate. The pivot mechanism 110 may be positioned at any location between a distal end 112 and a clamping end 114 of the cannula 100. As can be seen in FIG. 4, when the cannula 100 is in the closed condition, the base 102 and the arm 104 are brought together at the distal end 112 and at the clamping end 114. As can be seen in FIG. 5, when the cannula 100 is in the open condition, the base 102 and the arm 104 are moved apart from each other at the distal end 112 and at the clamping end 114. When being rotated from the closed condition to the open condition, the arm 104 and/or base 102 may be rotated as much as or more than 180 degrees.

The base 102 and the arm 104 may be pivotable around an axis 116 of the pivot mechanism 110 that extends in a first direction and may be adjacent to each other at the pivot mechanism 110 in the first direction. The first direction may be perpendicular to a longitudinal axis of the cannula 100. The base 102 and the arm 104 may also be adjacent to each other in the first direction at the distal end 112 but may be adjacent to each other in a second direction at the clamping end 114. The second direction may be different from the first direction. The second direction is preferably, but not necessarily, substantially perpendicular to the first direction. For example, FIG. 4 illustrates the base 102 and the arm 104 as being adjacent to each other at the pivot mechanism 110 in a side-by-side configuration (i.e., adjacent in the first direction). FIG. 4 also illustrates the base 102 and the arm 104 as being overlapped at the clamping end 114 in a stacked configuration (i.e., overlapped in the second direction). The base 102 and the arm 104 are preferably pivotable with respect to each other around only the axis 116.

Figure 1:
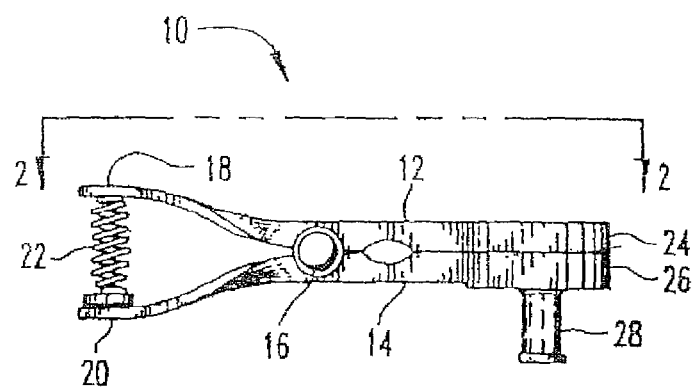
FIGS. 1-3 illustrate a cannula of the prior art.

As illustrated in FIGS. 4 and 5, there is preferably no biasing member (such as the spring 22 shown in FIG. 1) that biases the cannula 100 towards either a closed or open position. Such a lack of a biasing member may be advantageous in that the cannula 100 can be opened or closed, or adjusted to any position in between, and remain in that position without further action by a user. If such a biasing member were included, further structure, such as a brake or locking mechanism, could be included to achieve the advantage of the cannula 100 remaining in a position set by the user (other than the position dictated by the biasing member). A lack of biasing member may also allow the cannula 100 to open wider than if a biasing member is provided. For example, the spring 22 shown in FIG. 1 requires that the cannula 10 be squeezed to open, and there is limited travel between the handles 18 and 20, which results in a limited opening space between clamp heads 24 and 26. However, the cannula 100 shown in FIGS. 4-5 is not so limited. The cannula 100 has a squeeze-to-close action opposite of the squeeze-to-open action of the cannula 10. By including a squeeze-to-close action and no biasing member, the cannula 100 can be opened over a much wider range than is possible with the cannula 10 of FIG. 1. Also, such a squeeze-to-close configuration without a biasing member may allow for intermediate positions or stop points between a fully open position and a fully closed position. Any desired stop points may be provided with structure than tends to keep the cannula 100 in an intermediate position. Such structure could be achieved, for example, using detents (not shown). However, one of ordinary skill would appreciate that the cannula 100 could include a biasing member biasing the cannula 100 either open or closed if the needs of a user so dictate.

The base member 102 may include a first gripping portion 118 and a clamping portion 120. The first gripping portion 118 may extend from the distal end 112 of the cannula 100 to near the clamping members, e.g., the optional locking mechanism 106, and may be ergonomically configured to receive at least a first portion of a right and/or left hand of a user. The clamping portion 120 may be integrally formed with the base member 102 or may be a separately formed component. In addition, the clamping portion 120 may include an opening 122 through which an aortic patch or other type of vasculature of an organ may be fed. The clamping portion 120 may also include a first clamping surface 124 that is configured to cooperate with the floating clamp member 108 to clamp the aortic patch or other type of vasculature of the organ.

The arm member 104 may include a second gripping portion 126 and a floating clamp member seat 128. The second gripping portion 126 may extend from the distal end 112 of the cannula 100 to near the clamping members, e.g., the optional locking mechanism 106, and may be ergonomically configured to receive at least a second portion of the right and/or left hand of the user. The floating clamp member seat 128 may be configured to receive and support the floating clamp member 108.

The cannula 100 may preferably be configured to be operated (i.e., moved from the open condition to the closed condition or moved from the closed condition to the open condition) by one hand of the user. In addition, the cannula 100 may be ergonomically configured to be used by either a left hand or a right hand of the user. For example, in a left-handed configuration (as shown throughout the figures), the base 102 may be positioned to the right of the arm 104 at the pivot mechanism 110 when the cannula 100 is oriented so that the clamping end 114 is furthest from the user. Conversely, in a right-handed configuration (a mirror-image of what is shown throughout the figures), the base 102 may be positioned to the left of the arm 104 at the pivot mechanism 110 when the cannula 100 is oriented so that the clamping end 114 is furthest from the user.

The optional locking member 106 may lock the cannula 100 in the closed condition. Preferred embodiments may include a primary lock member 130, a toothed member 132 and an optional secondary lock member 134. The primary lock member 130 may be pivotally connected to the base 102 and may include an interacting portion 136, an unlocking portion 138 and a biasing portion 140. The interacting portion 136 may extend from the base 102 toward the toothed member 132 attached to the arm 104 and may pivot between a locked position and an unlocked position. The interacting portion 136 may include a hook-like portion 142 that may be positioned between the teeth of the toothed member 132. When the hook-like portion 142 is hooked to a tooth of the toothed member 132, the locking member 106 prevents the arm 104 from rotating open with respect to the base 102. It is contemplated that the toothed member 132 may be flexibly or pivotally attached to the arm 104. In either case, the toothed member 132 may be optionally biased. It is further contemplated that the primary lock member 130 may be pivotally connected to the arm 104 and the toothed member 132 may be flexibly or pivotally attached to the base 102.

The unlocking portion 138 may be connected to the interacting portion 136 at a pivot 144 so that when the unlocking portion 138 is pivoted around the pivot 144, the interacting portion is also pivoted around the pivot. The unlocking portion 138 is preferably positioned so that the base 102 is between the unlocking portion 138 and the interacting portion 136. Accordingly, pressing the unlocking portion 138 toward the base member 102 may cause the interacting portion 136 to move into the unlocked position. Conversely, allowing the unlocking portion 138 to pivot away from the base member 102 may cause the interacting portion 136 to move into the locked position.

The biasing member 140 is optional, and may be a spring-like element that extends from the interacting portion 136 toward the base 102. The biasing member may apply a biasing force that biases the interacting portion 136 toward the locked position.

Figure 6:
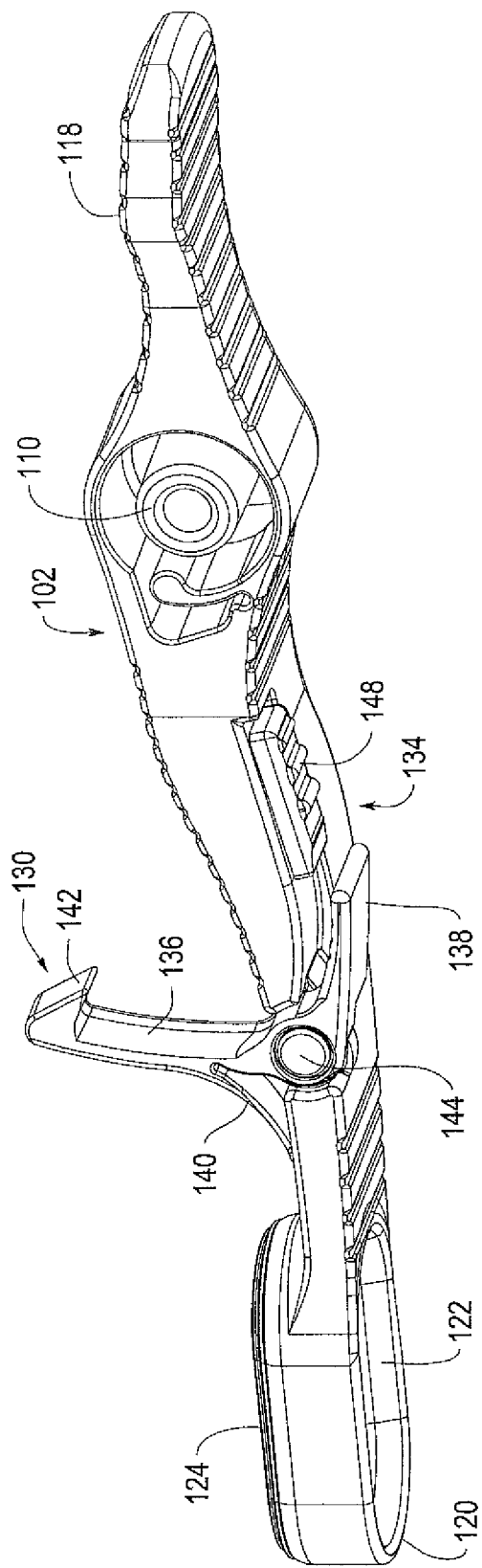
FIG. 6 illustrates an exemplary base member of the clamping apparatus of FIGS. 4 and 5.

The optional secondary lock member 134 may include a first sliding member 146 (as illustrated in FIG. 4) and a second sliding member 148 (as illustrated in FIG. 6). The first sliding member 146 may be positioned on the same side of the base 102 as the interacting portion 136. Positioning the first sliding member 146 in this manner may allow the optional secondary lock member 134 to be actuated by the user's thumb. The first sliding member 146 may be slidable toward and away from the interacting portion 136. The second sliding member 148 may be positioned on the same side of the base 102 as the unlocking portion 138 and may be slidable toward and away from the unlocking portion 138. The first and second sliding members 146 and 148 are connected to each other so that when the first sliding member 146 is moved in a particular direction, the second sliding member 148 is moved in the same direction. In addition, the second sliding member 148 is positioned so that when the second sliding member 148 is moved toward the unlocking portion 138, the second sliding member 148 is moved between the base 102 and the unlocking portion 138. This has the effect of preventing the unlocking portion 138 from being pressed toward the base 102. Accordingly, while the second sliding member 148 is between the unlocking portion 138 and the base 102, the interacting portion 136 cannot be moved to the unlocked position, and the cannula 100 cannot be moved from the closed condition to the open condition. This is advantageous because the cannula 100 is less likely to open unintentionally, which could result in the loss of or damage to an organ that has been cannulated.

The first sliding member 146 may be omitted from the secondary lock member 134. In an embodiment without the first sliding member 146, the user may operate the optional secondary lock member 134 by sliding the second sliding member 148, which may be accomplished with one of the user's fingers.

Figure 2:
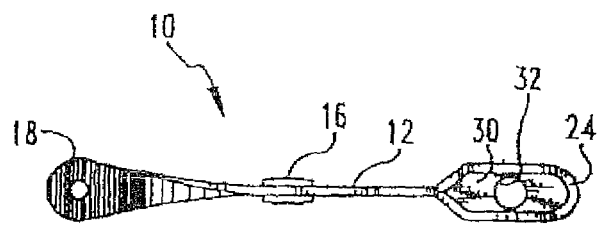
Figure 3:
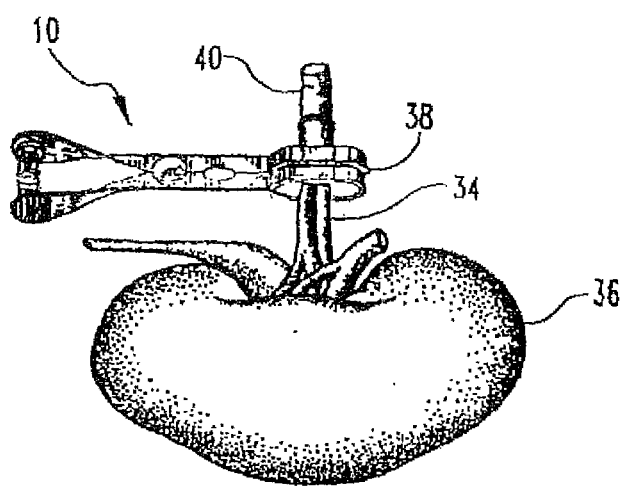
Figure 7A:
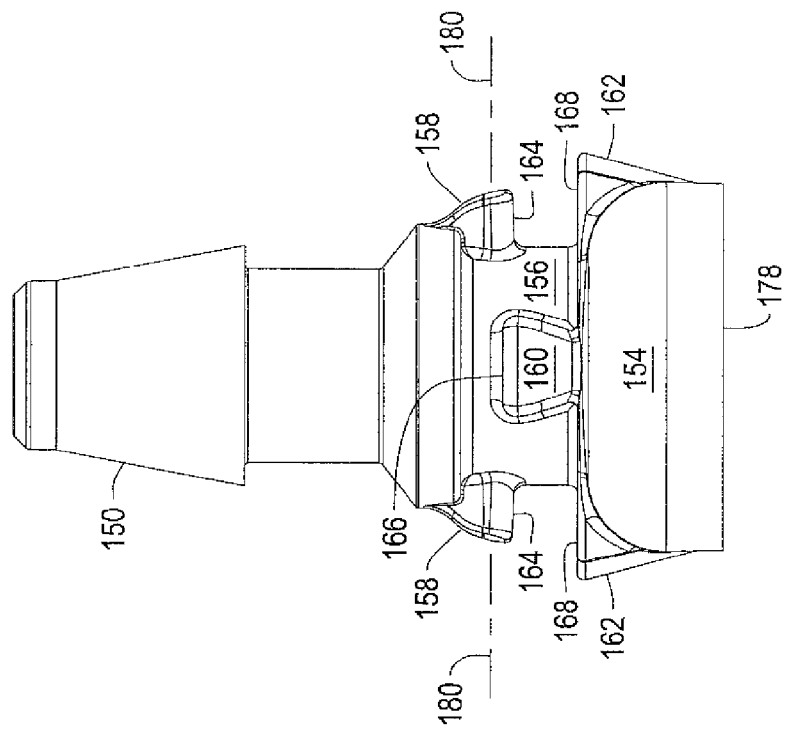
FIG. 7A illustrates an exemplary floating clamp member of the clamping apparatus of FIGS. 4 and 5.
Figure 7B:
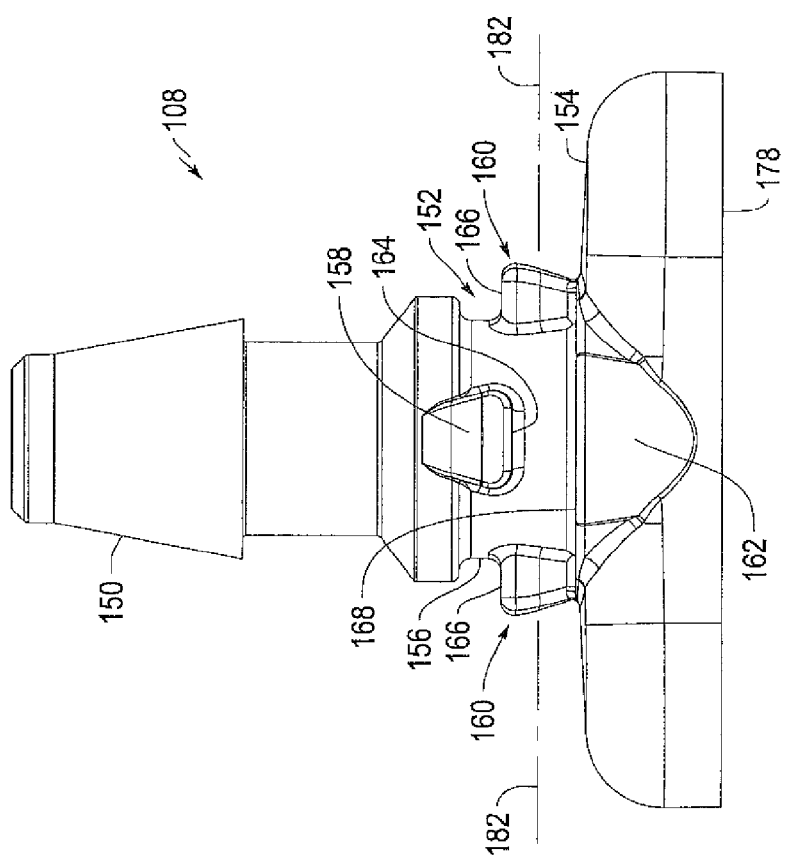
FIG. 7B illustrates another view of the floating clamp member of FIG. 7A.

As illustrated in FIGS. 7A and 7B the floating clamp member 108 may include a coupling portion 150, a support portion 152 and a cup portion 154. The coupling portion 150 may form a tubular structure and may provide a connection (such as a hose barb or luer lock) to a tube or other fluid conduit that connects the cannula 100 to the perfusion machine or system (not shown). Use of a hose barb or luer lock is advantageous because such structures are less likely to leak than the nipple 28 shown in FIGS. 1-3.

In embodiments, the cannula 100 may include features that allow for the second clamping surface 178 to change an angle relative to the first clamping surface 124 other than through movement of the base 102 and the arm 104. The change in relative angle can be about one or more axes. Such a change in angle can allow for the cannula 100 to clamp or cannulate varying thickness of tissue in a single blood vessel or the like that would otherwise prove troublesome with a cannula that does not allow for similar relative changes in angle between clamping surfaces. For example, with a cannula that does not allow for relative change in angle between clamping surfaces, it may be necessary to overly compress, and possibly damage, a blood vessel that is being cannulated or clamped in order to produce an adequate seal.

Alternatively, a seal that leaks may be required in order to avoid damage to the blood vessel.

In the depicted embodiment, the support portion 152 may include a plurality of features to connect the floating clamp member 108 to the arm 104. For example, the support portion may include a main body 156, upper primary support members 158, lower primary support members 160 and secondary support members 162. The upper primary support members 158 may be projections from the main body 156 and may each have a substantially horizontal bottom surface 164. The lower primary support members 160 may be positioned closer to the cup portion 154 than the upper primary support members 156 and may also be projections from the main body 156. The lower primary support members 160 may each have substantially horizontal top surfaces 166. The secondary support members 162 may be positioned closer to the cup portion 154 than the lower primary support members 160 and may also be projections from the main body 156. Alternatively, the lower primary support members 160 may be positioned closer to the cup portion 154 than the secondary support members 162. Either of these offset configurations may be advantageous in that when interacting with corresponding mating structure on the floating clamp member seat 128, two rotational degrees of freedom can be achieved while preventing a third rotational degree of freedom. The secondary support members 162 may each have horizontal top surfaces 168. The upper primary support members 158 may preferably be on opposite sides of the main body 156 from each other, the lower primary support members 160 may preferably be on opposite sides of the main body 156 from each other and/or the secondary support members 162 may preferably be on opposite sides of the main body 156 from each other. The upper primary support members 158 and the lower primary support members 160 may have similar or different shapes and sizes.

Figure 8:
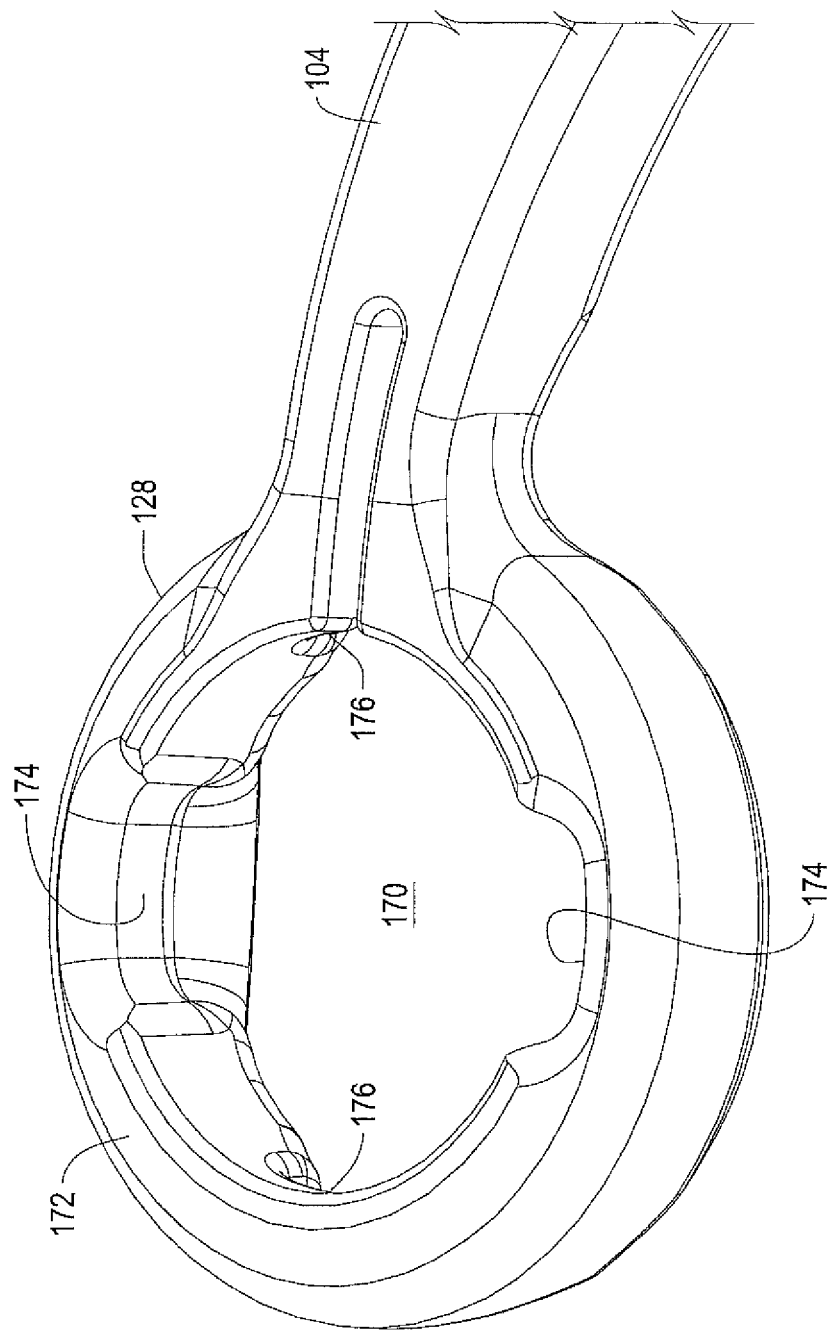
FIG. 8 illustrates an exemplary floating clamp member seat of the clamping apparatus of FIGS. 4 and 5.

As can be seen in FIG. 8, the floating clamp member seat 128 may include an opening 170 through which the floating clamp member 108 may be inserted and a support portion 172 surrounding the opening 170 that may support the floating clamp member 108. The support portion 172 may include a plurality of first recesses 174 and a plurality of second recesses 176. The first recesses 174 may each be configured to receive a corresponding upper primary support member 158. In addition, each first recess 174 may be shaped complementarily to the corresponding upper primary support member 158. For example, each of the first recesses 174 may be closed at the bottom and may be open at the top. The first recesses 174 may be sized to have a larger volume than the respective corresponding upper primary support members 158 so that the upper primary support members 158 may be free to move within the respective corresponding first recesses 174.

The second recesses 176 may each be configured to receive a corresponding lower primary support member 160. In addition, each second recess 176 may be shaped complementarily to the corresponding lower primary support member 160. For example, each of the second recesses 176 may be open at the bottom and may be closed at the top. The second recesses 176 may be sized to have a larger volume than the respective corresponding lower primary support members 160 so that the lower primary support members 160 may be free to move within the respective corresponding second recesses 176.

The configuration of the support portion 172 within the floating clamp member seat 128 may permit the floating clamp member 108 to rotate around more than one axis. For example, the floating clamp member 108 may rotate around an axis 180 that extends through centers of the upper primary support members 158. The axis 180 may extend along a plane that is parallel to a longitudinal axial plane of the cannula 100. The floating clamp member 108 may also rotate around an axis 182 that extends through centers of the lower primary support members 160. The axis 182 may also extend along a plane that is parallel to the longitudinal axial plane of the clamping apparatus. Other structures that allow at least two degrees of rotation between the floating clamp member 108 and the arm 104 are contemplated by the inventive principles discussed herein.

By permitting the floating clamp member 108 to rotate around two or more different axes, the orientation of a second clamping surface 178 may be variable with respect to the orientation of the first clamping surface 124. Accordingly, the cannula 100 may be more sensitive to variations in thickness of the tissue being clamped, thereby reducing the amount of damage to the tissue that may occur during the clamping process and reducing the likelihood that the grip will fail. Such rotation about two or more different axes also allows the first clamping surface 124 and the second clamping surface 178 to approach and/or engage one another, or engage clamped tissue, in a parallel fashion. In this manner, the entirety of each clamping surfaces will engage as near to simultaneously as practicable, which may result in more even application of clamping force and less likelihood of damage (or uneven damage) to clamped tissue. Evenly distributed clamping force may also be achieved, which may result in a superior seal versus clamping surfaces that cannot achieve such relative movement. Preferably, the floating clamp member 108 has a range of motion about each axis of about 15 degrees (7.5 degrees of positive and negative rotation for each axis) and more preferably about 12 degrees (6 degrees of positive and negative rotation for each axis) to avoid superfluous movement.

The cup portion 154 of the floating clamp member 108 may include the second clamping surface 178, which interacts with the first clamping surface 124 of the base 102 to clamp the tissue. As can be seen in FIG. 9, one clamping surface (e.g., the second clamping surface 178) may have a larger diameter than the other clamping surface (e.g., the first clamping surface 124). Although FIG. 9 illustrates the second clamping surface 178 having a larger diameter than the first clamping surface 124, it is contemplated that the first clamping surface 124 can have the larger diameter. In addition, one clamping surface may have a stepped shape along a perimeter, while the other clamping surface may have a shape complementary to the stepped shape of the one clamping surface in order to form a tighter seal around the clamped tissue. Alternatively, the first clamping surface 124 and the second clamping surface 178 may have similar cross-sectional shapes. It should be understood that, while in the closed position, the clamping surfaces can be in contact with each other or spaced apart a suitable distance (e.g., 0.5 mm to 4.00 mm, more preferably 1.0 mm to 3.0 mm) to accommodate tissue.

The cannula 100 can be made from any suitable material or materials, such as metal or transparent or opaque plastics, but plastics provide several advantages. Plastics are usually less costly, and can therefore be made disposable. A disposable version of the cannula 100 will not have the additional costs associated with reuse, such as re-sterilization.

Portions of the cannula 100 can be made from optically transparent material. This may be beneficial in that it can aid a clinician in positioning the vasculature and in detecting air bubbles or the interior or intima of the vasculature.

Either or both of the first clamping surface 124 and the second clamping surface 178 can include serrations and/or knurls to facilitate securing the clamped tissue. If the serrations or knurls are made from plastics, the plastics can be chosen with specific material properties to limit or prevent damage to clamped tissue. Additionally, serrations or knurls can be specifically tailored to the tissue to be clamped. The first clamping surface 124 and/or the second clamping surface 178 may include an elastomeric material to work in conjunction with and/or be substituted for the serrations and/or knurls.

While various features have been described in conjunction with the examples outlined above, various alternatives, modifications, variations, and/or improvements of those features and/or examples may be possible. Accordingly, the examples, as set forth above, are intended to be illustrative. Various changes may be made without departing from the broad spirit and scope of the underlying inventive principles.

What is claimed is:

1. A method of cannulating a blood vessel comprising:
   inserting the blood vessel through an opening within a first clamp member; and
   clamping a portion of the blood vessel between a first clamp surface of the first clamp member and a second clamp surface of a second clamp member,
   wherein:
      the first clamp surface applies a first force on the clamped portion of the blood vessel,
      the second clamp surface applies a second force on the clamped portion of the blood vessel, and
      the second clamp surface is configured to pivot relative to the first clamp surface such that a direction in which the second force is applied to the clamped portion of the blood vessel is able to change relative to a direction in which the first force is applied to the clamped portion of the blood vessel and that both the first clamp surface and the second clamp surface are configured to contact the blood vessel along each of their entire lengths when the second clamp surface is pivoted relative to the first clamp surface.

2. The method of claim 1, further comprising:
   moving a distal end of an arm member attached to the first clamp surface and a distal end of a base member attached to the second clamp surface toward each other to apply the first and second forces, the distal end of the arm member and the distal end of the base member being distal to the blood vessel.

3. The method of claim 2, wherein the first force and the second force are applied in opposing directions.

4. The method of claim 1, wherein an orientation of the second clamping surface is dependent on the shape of the surface of the clamped portion of the blood vessel.

5. The method of claim 4, wherein an orientation of the first clamping surface is independent of the shape of the surface of the clamped portion of the blood vessel.

6. The method of claim 1, further comprising locking the first and second clamp members in a clamping position in which the portion of the blood vessel is clamped between the first clamp surface and the second clamp surface.

7. The method of claim 6, wherein the first clamp member is attached to a base member and the second clamp member is attached to an arm member.

8. The method of claim 7, further comprising locking the arm and base members in the clamping position by pivoting one locking member to a locking position in which the one locking member interacts with another locking member.

9. The method of claim 1, further comprising making a fluid connection between the portion of the blood vessel and a perfusion apparatus by way of a fluid passage in the second clamp member.

\* \* \* \* \*